United States Patent [19]
Salzman et al.

[11] Patent Number: 5,958,427
[45] Date of Patent: Sep. 28, 1999

[54] NITRIC OXIDE DONOR COMPOUNDS AND PHARMACEUTICAL COMPOSITIONS FOR PULMONARY HYPERTENSION AND OTHER INDICATIONS

[76] Inventors: Andrew L. Salzman, 8280 Kugler Mill Rd., Cincinnati, Ohio 45243; Daniel J. Smith, 2988 Ridgeline Trail, Stow, Ohio 44224; Csaba Szabo, 3654 Stonebridge Dr., Apt. #E, Cincinnati, Ohio 45209; Richard J. Brilli, 43150 Ashley Meadow Ct., Cincinnati, Ohio 45227; Brian Krafte-Jacobs, 2216 Heather Hill Blvd., Cincinnati, Ohio 45244

[21] Appl. No.: 08/746,431

[22] Filed: Nov. 8, 1996

[51] Int. Cl.$^6$ ........................................ A61K 9/00
[52] U.S. Cl. ........................ 424/400; 424/45; 424/422; 424/426; 424/430; 424/433; 424/434; 424/435; 424/484; 514/551; 514/611; 514/929; 514/944; 514/946; 514/947
[58] Field of Search ................... 424/422, 426, 424/450, 430, 433, 434, 435, 451, 464, 484, 45; 514/929, 944, 946, 947, 551, 611, 642, 644, 664, 666, 667, 673, 674

[56] References Cited

U.S. PATENT DOCUMENTS

| | | | |
|---|---|---|---|
| 5,039,705 | 8/1991 | Keefer et al. | 514/611 |
| 5,155,137 | 10/1992 | Keefer et al. | 514/611 |
| 5,184,376 | 2/1993 | Diodati et al. | 514/611 |
| 5,208,233 | 5/1993 | Keefer et al. | 514/231.8 |
| 5,366,997 | 11/1994 | Keefer et al. | 514/611 |
| 5,389,675 | 2/1995 | Christodoulou et al. | 514/492 |
| 5,525,357 | 6/1996 | Keefer et al. | 424/486 |

OTHER PUBLICATIONS

*The Effect of Inhaled Nitric Oxide on the Pulmonary Circulation of the Neonatal Pig,* Nelin et al., Pediatric Research, vol. 35, No. 1, 1994.

*Nitric Oxide Reverses Acute Hypoxic Pulmonary Hypertension in the Newborn Piglet,* Etches et al., Pediatric Research, vol. 35, No. 1, 1994.

*Polycondensation of ω–Aminoalkylamino Acid Esters,* Fibers and Textiles Research Laboratories, Toray Industries, Inc. (1994).

*Secondary Amine/Nitric Oxide Complex Ions,* $R_2N$ [N(O)NO]–., J. Org. Chem. 1992 57, 6134–6138.

*Nitric Oxide Mediates Penile Erection in Cats,* Wang et al., The Journal of Urology, vol. 151, 234–237, Jan. 1994.

*Journal of Cardiovascular Pharmacology,* 25:674–678, 1995, Nitric Oxide (*NO*) Donor Molecules: Effect of NO Release Rate on Vascular Smooth Muscle Cell Proliferation In Vitro.

*Journal of Cardiovascular Pharmacology,* 31:55–62, 1996, Nebulized nitric oxide/nucleophile adduct reduces chronic pulmonary hypertension.

PCT International Search Report, International Application No. PCT/US97/20104, 5 pages, date of mailing: Apr. 6, 1998.

*Journal of Organic Chemistry,* vol. 58, No. 6, 1993, pp. 1472–1476, J. A. Hrabie et al., New Nitric Oxide–Releasing Zwitterions Derived from Polyamines.

*Primary Examiner*—Neil S. Levy
*Attorney, Agent, or Firm*—Wood, Herron & Evans, L.L.P.

[57] ABSTRACT

The invention is directed to nitric oxide (NO) donor compounds and to pharmaceutical compositions containing such nitric oxide (NO) donor compounds, for delivering NO to the apical surface of a mucosa, where the nitric oxide is released for passage across the epithelial monolayer of the mucous membrane. The NO donor compounds include polyalkyleneamine NO donors as well as tertiary and quaternary amino aliphatic NO donor compounds. The compounds and compositions of the invention are useful in any situation in which it is desirable to deliver NO across a mucosal surface. For example, the compounds and compositions of the invention are particularly useful in treating pulmonary hypertension, male impotence, and several other specific conditions.

28 Claims, 5 Drawing Sheets

NITRIC OXIDE DONOR COMPOUNDS AND PHARMACEUTICAL COMPOSITIONS FOR PULMONARY HYPERTENSION AND OTHER INDICATIONS

BACKGROUND OF THE INVENTION

1. Field of the Invention

This invention relates to nitric oxide donor compounds and, more particularly, to such compounds and their pharmaceutical compositions for use in delivering nitric oxide to the apical surface of a mucosa, where the nitric oxide is released for passage across the epithelial monolayer of the mucous membrane. The invention also relates to the treatment of specific conditions and disorders in which the local delivery of nitric oxide has a salutory effect. Such conditions and disorders include, for example, pulmonary hypertension and impotence, which benefit from the invention's ability to cause local vasodilation without causing a similar vasodilation of the systemic vasculature.

2. Description of the Related Art

Pulmonary hypertension is a serious medical condition. Acute pulmonary hypertension, resulting from a deficiency of nitric oxide (NO) production in the pulmonary vasculature or from a non-NO related process, increases pulmonary capillary pressure, augments transvascular flux, and increases right ventricular afterload. Additionally, in the presence of right to left anatomic extrapulmonary shunts or intrapulmonary physiologic shunts, pulmonary hypertension may contribute to systemic desaturation. Chronic pulmonary hypertension also may induce remodeling of the pulmonary vasculature, inducing an irreversible smooth muscle hypertrophy.

In addition to being quite serious, pulmonary hypertension is frequently encountered, resulting from a number of conditions, including for example, adult respiratory distress syndrome, neonatal respiratory distress syndrome, pneumonia, asthma, bronchiolitis, chronic obstructive pulmonary disease, restrictive lung disease, near drowning, cardiopulmonary arrest, cardiopulmonary bypass, emphysema, sepsis, infection, shock, congenital heart disease and congenital diaphragmatic hernia.

Recently, NO has been shown to be a useful agent in the treatment of pulmonary hypertension when delivered in its gaseous form to the lung via an endotracheal route during mechanical ventilation. Nelin L, Moshin C, Sasidharan T, Dawson C, "The effect of inhaled nitric oxide on the pulmonary circulation of the neonatal pig," *Pediatric Research* 1994, 35:20–24; Etches P, Finer K, Barrington A, Graham A, Chan W, "Nitric oxide reverses acute hypoxic pulmonary hypertension in the newborn piglet," *Pediatric Research* 1994, 35:15–19. Although the exact mechanism by which inhaled NO dilates the pulmonary vascular bed is unknown, it is presumed that NO is distributed to distal ventilated alveolar segments, where it passes readily due to its great lipophilicity, through the epithelium into the interstitial space. From there, NO passes through the vascular adventitia and reaches the cytosol of the arteriolar vascular smooth muscle, where it interacts with iron in the heme center of guanylyl cyclase. NO binding induces a conformational change in the enzyme which permits the catalysis of GTP to cGMP, with a subsequent alteration in intracellular calcium and vascular smooth muscle relaxation. NO, which instead passes through the vascular smooth muscle and endothelium and into the vascular lumen, is believed to be inactivated by its interaction with the iron center in hemoglobin. In this manner, NO is believed to be a selective pulmonary vasodilator, since it becomes immediately ineffective in the systemic circulation. Although some recent evidence suggests that NO may circulate as a relatively stable adduct, in the form of a nitrosylated hemoglobin species, which could in theory cause systemic vasodilation, in practice, inhaled NO does not appear to have any direct effect on systemic vascular resistance.

Although inhalation of nitric oxide gas has been shown useful in the treatment of pulmonary hypertension, there are several drawbacks and limitations with this particular mode of therapy. For example, this therapy requires large gas tanks, expensive monitoring equipment, and a highly skilled technician to operate the tanks and equipment and deliver the NO gas to a patient. Therefore, this mode of treatment is generally limited to a hospital or other clinical setting and, even then, is inconvenient and relatively expensive. Given the seriousness and incidence of pulmonary hypertension, there is a great need for a more flexible, less expensive mode of treatment, in which a vasodilator such as NO may be delivered to the lung without causing undesirable systemic vasodilation.

Another NO-mediated condition is impotence, that is, the inability of a male to achieve or maintain an erection. Penile erection involves parasympathetic, neuronally mediated relaxation of the blood vessels and the trabecular meshwork of smooth muscle that constitutes the *corpora cavernosa*. The relaxation of the cavernous smooth muscle plays a critical role in erection, which is largely nerve-mediated by a nonadrenergic, noncholinergic (NANC) mechanism; however, endothelium-dependent cholinergic neurotransmission may also mediate penile erection. Recent studies have shown that nitric oxide (NO) is the major neuronal mediator of erection. Several in vitro studies have demonstrated that NO is responsible for the relaxation of rabbit and human *corpus cavernosum* smooth muscle strips. In vivo studies in rats and dogs also demonstrated that NO is the principal neurotransmitter in cavernous smooth muscle relaxation. Wang R, Domer F R, Sikka S C, Kadowitz P J, Hellstrom W J G, "Nitric oxide mediates penile erection in cats," *The Journal of Urology* 1994, 151:234–237. In the past, treatment options for impotence have included direct smooth muscle vasodilators such as papaverine and vasodilator prostaglandins, such as $PGE_2$, to name a few. More recently, the NO donors s-nitrosocysteine (NO-CYS) and s-nitroso-n-acetylpenicillamine (SNAP) have been proposed for therapeutic use. Id. However, since the safety and long-term effects of NO-CYS and SNAP have yet to be studied in human clinical trials, it would be extremely beneficial to develop additional therapies.

SUMMARY OF THE INVENTION

In order to overcome the limitations of the related art discussed above, we have developed several nitric oxide donor compounds, as well as several pharmaceutical compositions. These compounds have proven beneficial in the treatment of pulmonary hypertension and in mediating penile erection, and we believe these compounds and compositions to be beneficial in the treatment of several additional conditions and disorders.

The NO donor compounds include tertiary and quaternary amino aliphatic NO donor compounds having one of the following structures:

-continued or a salt thereof, wherein

X and X' are independently selected from the group consisting of oxygen, alkylene, alkenylene and Y is selected from the group consisting of alkyl and substituted alkyl;

Z is selected from the group consisting of and alkylene;

$R_1$, $R_2$, $R_3$, $R_1'$, $R_2'$, and $R_3'$ are independently alkyl; and n is an integer from 2 to 6.

The NO donor compounds also include branched and unbranched polyalkyleneamine nonoates. Examples of such nonoates include polyethyleneamine nonoate and polyisopropyleneamine nonoate.

The pharmaceutical compositions of the invention include a mucosally impermeant nitric oxide donor compound and a physiologically acceptable carrier. As used herein, the term "mucosally impermeant" refers to the reduced ability, and even inability of a compound to pass through a mucous membrane. These mucosally impermeant compounds include:

(1) the 12 tertiary and quaternary amino aliphatic NO donor compounds in the group of twelve structures listed above; and (2) polyalkyleneamine nonoates.

These compounds and compositions will find benefit in treating a number of conditions which require local vasodilation without dilating the systemic vasculature. Examples of such conditions include pulmonary hypertension, impotence, vaginal drying and insufficient blood flow to the gastrointestinal tract. In addition, the compounds and compositions of the invention will find benefit as an antibacterial in the mouth and as an aphrodisiac when applied topically to the genitalia.

These and other benefits and advantages will become readily apparent to one of ordinary skill in the art upon a review of the following figures and detailed description of several preferred embodiments of the invention.

DETAILED DESCRIPTION OF SEVERAL PREFERRED EMBODIMENTS OF THE INVENTION

This invention is directed to several compounds and pharmaceutical compositions, as well as to methods of using these compounds and compositions in nitric oxide-mediated conditions.

The compounds include tertiary and quaternary amino aliphatic nitric oxide donor compounds having one of the following structures:

-continued (XI)

(XII)

or a salt thereof, wherein

X and X' are independently selected from the group consisting of oxygen, alkylene, alkenylene and Y is selected from the group consisting of alkyl and substituted alkyl;

Z is selected from the group consisting of and alkylene;

$R_1$, $R_2$, $R_3$, $R_1'$, $R_2'$, and $R_3'$ are independently alkyl; and n is an integer from 2 to 6.

As used herein, the term "salt" refers to any pharmaceutically acceptable salt, including, for example, an intramolecular salt, an intermolecular salt or a pharmaceutically acceptable (i.e., nontoxic) cation. By way of further example, an intramolecular salt may be formed between the negative charge on the NONO⁻ portion (also known as the "nonoate moiety") of the molecule and a positive charge on one of the amino nitrogens of the same molecule. Similarly, an intermolecular salt may be formed between the negative charge on the nonoate moiety of one molecule and a positive charge on an amino nitrogen of an adjacent molecule.

In a preferred form of the invention, the tertiary or quaternary amino aliphatic nitric oxide donor compound is water soluble, i.e., soluble in physiological mediums. Particularly preferred compounds include 2-(dimethylamino) ethylputreanate nonoate, 2-(diethylamino)ethylputreanate nonoate and the propyl homolog of 2-(dimethylamino) ethylputreanate nonoate. In the propyl homolog, the "putreanate" portion of the molecule includes a propyl group, in lieu of the butyl group. These preferred compounds can be made as taught in Working Examples 1–3, below. In addition, the tertiary amino aliphatic NO donor compound di(2-(dimethylamino)ethyl)spermate nonoate can be made as taught in Example 4. The term "nonoate" refers to a compound which includes an $N_2O_2^-$ moiety (a nonoate moiety) and which is capable of releasing nitric oxide under physiological conditions.

The compounds also include straight-chain (unbranched) and branched polyalkyleneamine (PAA) nonoates. In a preferred form of the invention, the PAA nonoate has a molecular weight of about 5,000 to about 100,000, more preferably, about 10,000 to about 25,000. Preferred PAA nonoates include polyethyleneamine nonoate and polyisopropyleneamine nonoate, in either branched or unbranched form.

The use of these compounds is discussed in detail below.

The pharmaceutical compositions of the present invention are compositions for delivering an NO donor compound to the apical surface of a mucosa. These compositions include a mucosally impermeant NO donor compound and a physiologically acceptable carrier. As used herein, the term "mucosally impermeant" refers to the reduced ability, and even inability, of a particular compound to cross a mucous membrane.

The mucosally impermeant NO donor compounds include:

(1) the tertiary and quaternary amino aliphatic NO donor compounds in the group of twelve structures listed above; and (2) polyalkyleneamine nonoates.

While not intending to be bound by any particular theory, we have found that the compounds and compositions of the invention are successful as delivery vehicles for NO and in site-specific vasodilation because of their ability to release nitric oxide at the epithelial boundary of the mucosa, without crossing the epithelial boundary themselves. With respect to the tertiary and quaternary amino aliphatic NO donor compounds (which include the compounds in the group of the twelve structures listed above having at least one tertiary or quaternary amino end group, as well as the polyalkyleneamines), these compounds are restricted from crossing the epithelial boundary due to their polarity. In particular, at physiological pH, at least one of the tertiary or quaternary nitrogens in these compounds has a dedicated positive charge, which restricts the particular compound from passing through the mucosal membrane. Therefore, the mucosally impermeant compounds of the invention are restricted by the epithelial monolayer, due to charge and polarity, and thus, they cannot cross into the systemic circulation and cause systemic hypotension. The nitric oxide moiety attached to the particular NO donor compound, however, is released over time and does diffuse, by virtue of its lipophilic nature, across the epithelium and into the desired local vascular bed, thereby causing a local vasodilation. We have thus designed a system whereby nitric oxide may be delivered for a particular period of time following a single administration, without the need for instrumentation, calibration systems, gas tanks, scavengers and the like.

The compounds of the invention are made as follows. With respect to the tertiary and quaternary amino aliphatic NO donor compounds having a tertiary or quaternary amino end group, these compounds are made as taught in Examples 1–4, below. The polyalkyleneamine nonoates are made as taught in Example 5. Preferred polyalkyleneamine NO donor compounds include polyethyleneamine nonoate and polyisopropyleneamine nonoate. As seen in Example 5, these NO donor compounds are made by starting with the appropriate commercially available polyalkyleneamine. As one of ordinary skill will recognize, although these starting materials are truly polyalkyleneamines, they are frequently referred to as polyalkyleneimines. For example, polyethyleneamine is frequently referred to as polyethyleneimine or "PEI", and polyisopropyleneamine is often referred to as polyisopropyleneimine or "PPI", even though both are amine compounds. As commercially available, both PEI and PPI contain a mixture of amines. More specifically, it is believed that within each compound, about 50% of the amino groups are tertiary, about 25% are secondary, and about 25% are primary.

The compounds and compositions of the invention are useful in any situation where it is desirable to deliver nitric oxide across a mucous membrane. For example, as seen in Example 6, the compounds and compositions are particularly useful in the treatment of pulmonary hypertension. When used to treat pulmonary hypertension, the compounds preferably are used as inhaled agents to be delivered to the tracheobronchial tree and distal alveoli for the purpose of locally dilating the pulmonary vascular bed, thereby reducing pulmonary hypertension. Depending upon the patient setting and needs of the particular patient, the compound may suitably be delivered in the form of an aerosol or nose drops. Also, the particular compound may be delivered by a device inserted into the oropharynx or nasopharynx, or via an endotracheal tube in patients with a tracheostomy or in patients who are intubated. In addition, if an aerosol is used, a device such as a metered dose inhaler may be used to deliver the aerosol.

In a preferred form of the composition, the compound is combined with saline, with the composition having a concentration of about 1 mg/ml to about 250 mg/ml of compound to saline. Alternatively, other carriers may be used, either alone or in combination, as is known in the art. Such carriers may include Ringers-Lactate, water, dimethyl sulfoxide, sodium hydroxide, ethanol, a colloid solution, a crystalloid solution, dextrose, albumin, a surfactant, and the like. In addition, depending upon the particular needs of the patient, the compound may suitably be administered at a dose of from about 1 mg/kg body weight to about 50 mg/kg body weight.

As seen in Example 7, the compounds of the invention also are useful in treating male impotence. For this indication, the compounds suitably are formulated as topical agents for external application to the skin or, preferably, for intraurethral administration. Preferably, the composition is formulated as a hydrophilic gel, as is known in the art. With respect to dosing, the compound may suitably be administered at a dose of from about 1 mg/kg body weight to about 50 mg/kg body weight.

The compounds also are believed to be useful in inhibiting or treating vaginal drying. The compounds are believed to be useful for this indication because the secretion of a fluid by a mucosal membrane is regulated, in part, by cyclic GMP in the cell, and because NO is a known mediator of guanylyl cyclase, an enzyme which forms cyclic GMP. Therefore, when an NO donor compound of the invention is administered to the mucosal surface of the vagina, it is believed that fluid is secreted by the mucosa into the lumen, thereby providing lubrication. And, because the donor compounds do not cross into the systemic vasculature, lubrication is achieved without inducing systemic hypotension. Preferably, compositions for the vaginal drying indication are formulated as a hydrophilic gel for topical or intraurethral administration. In addition, the compound itself may suitably be administered at a dose of from about 1 mg/kg body weight to about 50 mg/kg body weight.

The compositions of the invention also may be used for a number of additional indications. For example, the compounds are useful for stimulating blood flow to an epithelial mucosal surface of the gastrointestinal tract. For this use, the compounds preferably are formulated for parenteral administration. The compounds also may be used as an aphrodisiac by applying them topically to the genitalia. The nitric oxide donor compounds also are useful as antibacterial agents in the mouth. Nitric oxide is known to kill or inactivate several strains of bacteria, many of which are found in the mouth. Accordingly, the NO donor compounds are useful as antibacterial agents in the mouth. Preferably, when NO donor compounds are used for this indication, they are formulated as a mouth wash.

The following examples are provided by way of illustration, and are not intended to limit the scope of the invention.

EXAMPLES 1–5

The Synthesis of Specific NO Donor Compounds

Example 1

Synthesis of 2-(dimethylamino)ethylputreanate nonoate

A. Synthesis of 2-(dimethylamino)ethylputreanate

The starting materials, 2-(dimethylamino)ethylacrylate and 1,4-diaminobutane were purchased 99% pure from Aldrich and used without further purification. Tetrahydrofuran (THF) was purchased from Fisher and was distilled over sodium metal and benzophenone prior to use.

The monoester compound, 2-(dimethylamino) ethylputreanate, was synthesized by first dissolving 5.0 g of 2-(dimethylamino)ethylacrylate into 100 ml of THF. This was then added dropwise by an addition funnel to a 5 molar excess of 1,4-diaminobutane in 100 ml of THF contained in a 200 ml round bottomed flask over an eight hour period with constant and vigorous stirring. The reaction was vigorously stirred at room temperature for an additional eight hours at which time the completion of the reaction was confirmed by $^1$H NMR. Isolation of the compound was begun by stripping the THF by rotary evaporation to a yellow oily product. Subsequent drying of the 2-(dimethylamino)ethylputreanate was done in a vacuum oven at room temperature overnight.

B. Synthesis of 2-(dimethylamino)ethylputreanate nonoate

The NO modified compound was prepared by dissolving 3 ml of 2-(dimethylamino)ethylputreanate in 80 ml of THF in a high pressure glass bottle (Ace Glass). The mixture was purged with nitrogen gas ($N_2$) at 12 psi and then with NO gas at 12 psi. The NO pressure was increased to 70 psi and stirred vigorously. The completion of the reaction occurred within 18 hours and was monitored by observing the absorbance at 240 nm and confirmed by $^1$H NMR. The pressure was released carefully and the liquid layer was decanted. Four hundred mg of the nonoate accumulated as a wax on the walls of the reaction flask. The wax was stored in the freezer under $N_2$ gas.

A release profile was performed by adding 5 mg of the NO modified compound to 50 ml of phosphate buffered saline (pH 7.4). A sample was immediately placed in a quartz cuvette which was introduced to an HP 8452A diode array Spectophotometer. The amount of liberated NO was determined by measuring the decrease of the absorbance of NO modified compound at a wavelength of 250 nm over time.

Figure 1:
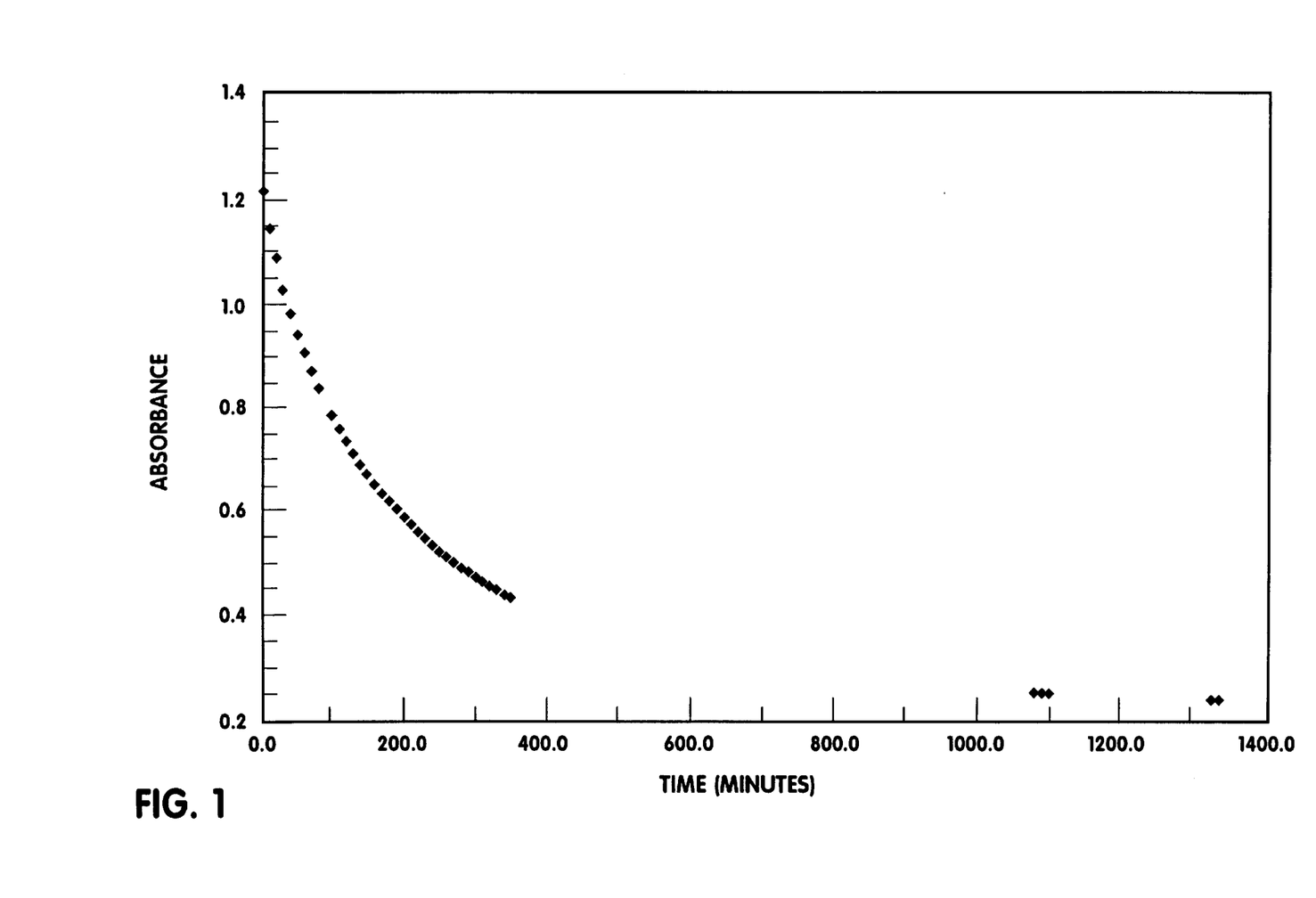
FIG. 1 is a release profile for 2-(dimethylamino) ethylputreanate nonoate.

Initially, measurements were taken every 10 minutes for 6 hours until the release rate decreased. Additional measurements were taken at 18 and 22 hours. The release data were then used to compile the release profile shown in FIG. 1, which displays the decrease in absorbance of the NO modified compound over time.

Example 2

Synthesis of 2-(diethylamino)ethylputreanate nonoate

A. Synthesis of 2-(diethylamino)ethylputreanate

The starting materials, 2-(diethylamino)ethylacrylate and 1,4-diaminobutane were purchased 99% pure from Aldrich and used without further purification. Tetrahydrofuran (THF) was purchased from Fisher and was distilled over sodium metal and benzophenone prior to use.

The monoester compound, 2-(diethylamino) ethylputreanate, was synthesized by first dissolving 5.0 g of 2-(diethylamino)ethylacrylate into 100 ml of THF. This was then added dropwise by an addition funnel to a 5 molar excess of 1,4-diaminobutane (14.5 ml) in 100 ml of THF contained in a 250 ml round bottomed flask over an eight hour period with constant and vigorous stirring. The reaction was vigorously stirred at room temperature for an additional eight hours at which time the completion of the reaction was confirmed by $^1$H NMR. Isolation of the compound was begun by stripping the THF by rotary evaporation to a yellow oily product. Subsequent drying of the 2-(diethylamino)ethylputreanate was done in a vacuum oven at room temperature overnight.

B. Synthesis of 2-(diethylamino)ethylputreanate nonoate

The NO modified compound was prepared by dissolving 2 ml of 2-(diethylamino)ethylputreanate in 80 ml of THF in a high pressure glass bottle (Ace Glass). The mixture was purged with nitrogen gas ($N_2$) at 12 psi and then with NO gas at 12 psi. The NO pressure was increased to 70 psi and stirred vigorously. The completion of the reaction occurred within 18 hours and was monitored by observing the absorbance at 240 nm and confirmed by $^1$H NMR. The pressure was released carefully and the liquid layer was decanted. Four hundred mg of the nonoate accumulated as a wax on the walls of the reacion flask. The wax was stored in the freezer under $N_2$ gas.

Example 3

Synthesis of the Propyl Homolog of 2-(dimethylamino)ethylputreanate nonoate

A. Synthesis of the propyl homolog of 2-(dimethylamino) ethylputreanate

The starting materials, 2(dimethylamino)ethylacrylate and 1,3-diaminopropane were purchased 99% pure from Aldrich and used without further purification. Tetrahydrofuran (THF) was purchased from Fisher and was distilled over sodium metal and benzophenone prior to use.

The monoester compound, the propyl homolog of 2-(dimethylamino)ethylputreanate, was synthesized by first dissolving 5.0 g of 2-(dimethylamino)ethylacrylate into 100 ml of THF. This was then added dropwise by an addition funnel to a 5 molar excess of 1,3 diaminopropane (about 15 ml) in 100 ml of THF contained in a 250 ml round bottomed flask over an eight hour period with constant and vigorous stirring. The reaction was vigorously stirred at room temperature for an additional eight hours at which time the completion of the reaction was confirmed by $^1$H NMR. Isolation of the compound was begun by stripping the THF by rotary evaporation to a yellow oily product. Subsequent drying of the propyl homolog of 2-(dimethylamino) ethylputreanate was done in a vacuum oven at room temperature overnight.

B. Synthesis of the propyl homolog of 2-(dimethylamino) ethylputreanate nonoate

The NO modified compound was prepared by dissolving 3 ml of the propyl homolog of 2-(dimethylamino) ethylputreanate in 80 ml of THF in a high pressure glass bottle (Ace Glass). The mixture was purged with nitrogen gas ($N_2$) at 12 psi and then with NO gas at 12 psi. The NO pressure was increased to 70 psi and stirred vigorously. The completion of the reaction occurred within 18 hours and was monitored by observing the absorbance at 240 nm and confirmed by $^1$H NMR. The pressure was released carefully and the liquid layer was decanted. Four hundred mg of the nonoate accumulated as a wax on the walls of the reaction flask. The wax was stored in the freezer under $N_2$ gas.

A release profile was performed by adding 5 mg of the NO modified compound to 50 ml of phosphate buffered saline (pH 7.4). A sample was immediately placed in a quartz cuvette which was introduced to an HP 8452A diode array Spectophotometer. The amount of liberated NO was determined by measuring the decrease of the absorbance of NO modified compound at a wavelength 250 nm over time.

Figure 2:
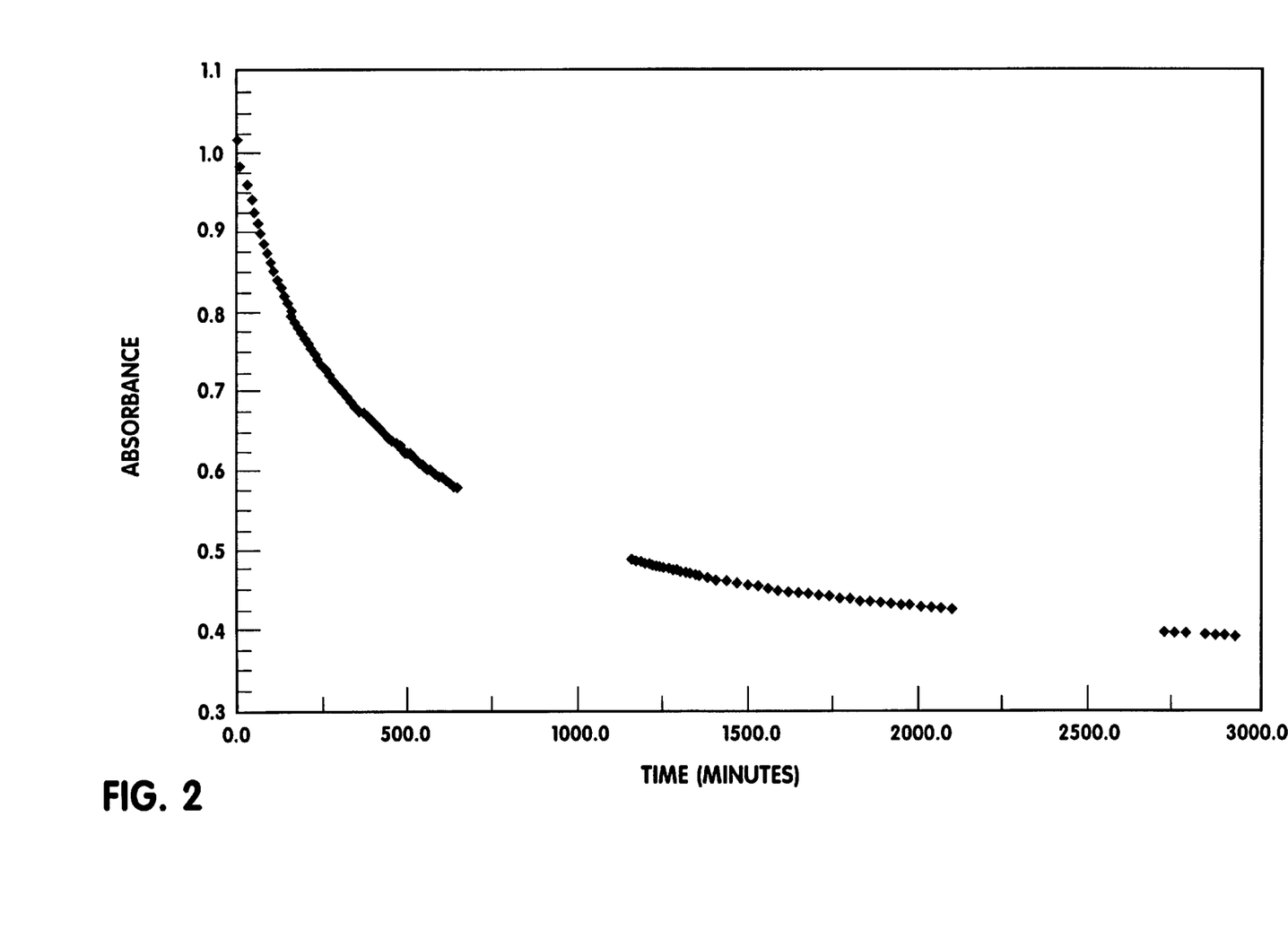
FIG. 2 is a release profile for the propyl homolog of 2-(dimethylamino)ethylputreanate nonoate.

Initially, measurements were taken every 10 minutes for 11 hours until the release rate decreased. Additional measurements were taken once every 10 minutes for hours 19 through 23, then every 30 minutes for the next 12 hours. The release data were then used to compile the release profile shown in FIG. 2, which displays the decrease in absorbance of the NO modified compound over time.

Example 4

Synthesis of di(2-(dimethylamino)ethyl)spermate nonoate

A. Synthesis of di(2-(dimethylamino)ethyl)spermate

The starting materials 2-(dimethylamino)ethylacrylate and 1,4-diaminobutane were purchased 99% pure from Aldrich and used without further purification. Tetrahydrofuran (THF) was purchased from Fisher and was distilled over sodium metal and benzophenone prior to use.

The diesterified compound, di(2-(dimethylamino)ethyl) spermate, was synthesized by first dissolving 2.0 g of 2-(dimethylamino)ethylacrylate into 50 ml of THF. This was then added dropwise by an addition funnel to 0.5 equivalents of 1,4-diaminobutane in 50 ml of THF contained in a 200 ml round bottomed flask over an eight hour period with constant and vigorous stirring. The reaction was stirred continuously at room temperature for an additional eight hours. The completion of the reaction was confirmed by $^1$H NMR. Isolation of the compound was begun by stripping the THF by rotary evaporation with subsequent drying in a vacuum oven at room temperature overnight.

B. Synthesis of di(2-(dimethylamino)ethyl)spermate nonoate

The NO modified compound was prepared by dissolving 150 mg of di(2-(dimethylamino)ethyl)spermate in 80 ml of THF in a high pressure glass bottle (Ace Glass). The mixture was purged with nitrogen gas ($N_2$) at 12 psi and then with NO gas at 12 psi. The NO pressure was increased to 70 psi and stirred vigorously. The completion of the reaction occurred within 18 hours and was monitored by observing the absorbance at 240 mn and confirmed by $^1$H NMR. The pressure was released carefully and the liquid layer was decanted. Five hundred mg of the nonoate accumulated as a wax on the walls of the reaction flask. The wax was stored in the freezer under $N_2$ gas.

Example 5

Synthesis of polyethyleneamine nonoate

Polyethyleneamine (PEA), commonly referred to as polyethyleneimine (PEI), and anhydrous grade acetonitrile were purchased from Aldrich Chemical Company. Both were used without further modification.

2.0 g of PEA (Av. MW. 25000) were dissolved in 70 ml of acetonitrile which produced a cloudy mixture. The mixture was placed into a high pressure bottle (Ace Glass) equipped with a magnetic stir bar. The chamber was evacuated with a vacuum pump and then NO was introduced at 80 psi for ½ hour. The chamber was sealed and allowed to stand at 80 psi for 24 hours. The mixture was then again exposed to NO at 80 psi for ½ hour and the resealed chamber was allowed to stand for another 24 hour period at 80 psi. Once again, new NO was introduced into the system at 80 psi for ½ hour at which time the system was resealed and allowed to stand for an additional 24 hour period at 80 psi.

The resulting NO modified compound, PEA nonoate, precipitated out of the solution as a yellow solid that adhered to the sides of the bottle. The acetonitrile was decanted off. 1.85 g of the precipitate was collected and then washed with anhydrous ethanol and then with anhydrous diethyl ether. The NO modified compound was allowed to stand at room temperature for 12 hours.

The release profile on the PEA nonoate was measured using a Monitor Labs model 8440 Nitric Oxide Analyzer interfaced with an HP 3396 A Chromatography Integrator. The analyzer was connected to an impinger bottle (Ace Glass) containing 5.0 mg of the compound in 25 ml of phosphate buffered saline (pH 7.4). The impinger bottle had one way Teflon stopcock valves attached in order to prevent the escape of any generated nitric oxide. Teflon flow meters were inserted at the beginning of the circuit, and just before entry into the analyzer.

Figure 3:
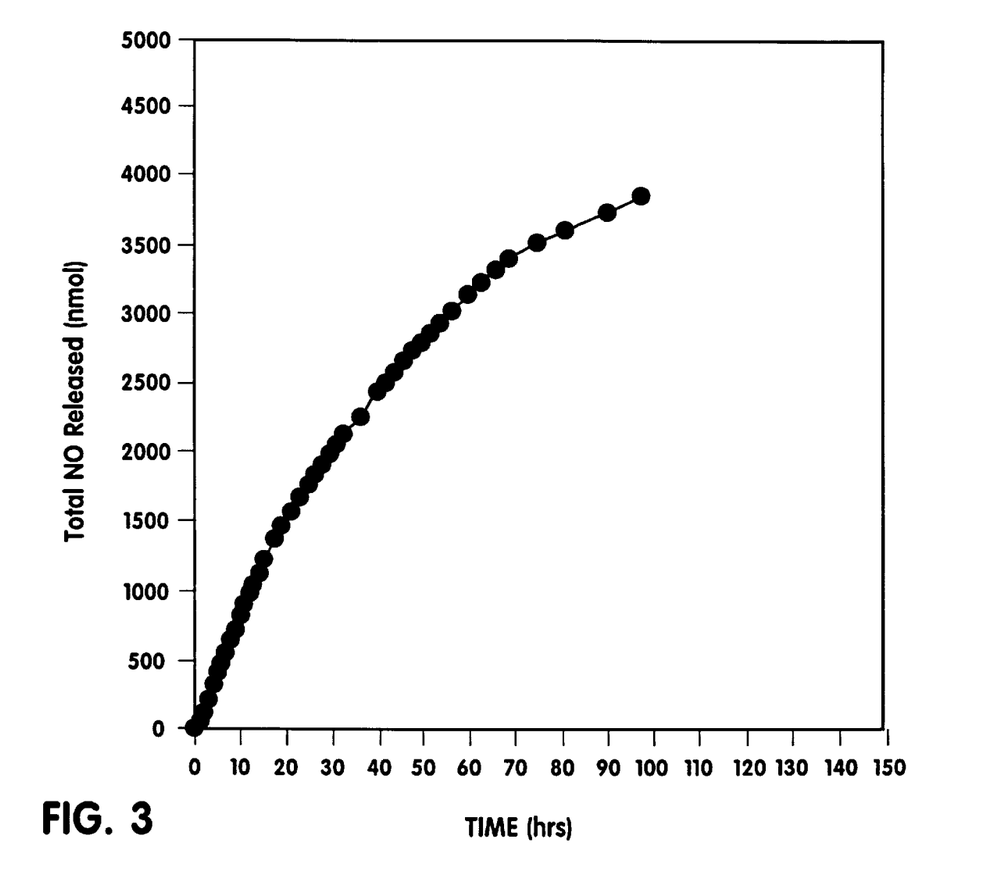
FIG. 3 is a release profile for polyethyleneamine nonoate.

The contents of the bottle were continuously stirred and the system was flushed with helium at 12 psig into the analyzer. Measurements were taken at arbitrary time intervals for 72 hours. The release data was then used to compile the release profile shown in FIG. 3.

Example 6

Treatment of Pulmonary Hypertension in in Vivo Model using 2-(dimethylamino)ethylputreanate nonoate Male, immature, random-bred Yorkshire pigs (6–10 weeks old, 10–15 kg body weight) were anesthetized and received mechanical ventilatory support. General anesthesia was maintained with nitrous oxide and isoflurane. (Nitrous oxide is a distinct chemical species which does not have the properties of the free radical nitric oxide). Minute ventilation was adjusted to maintain $PaCO_2$ at 40±5 torr and pH from 7.35 to 7.45. A femoral cutdown was performed for insertion of femoral venous and arterial catheters. A midsternotomy was performed and a 16 mm cardiac output flow probe was positioned around the pulmonary artery. Catheters were inserted into the right atrium, left atrium, and pulmonary artery for pressure measurement and were secured with a purse-string suture.

Hemodynamic measurements were obtained as follows: Mean arterial pressure (MAP), mean pulmonary pressure (MPAP), left atrial pressure (LAP), and right atrial pressure (RAP) were determined using calibrated transducers driving an amplifier monitor with digital readout. Heart rate was recorded with a pulse oximeter. Cardiac output was recorded from the digital readout of the flowmeter connected to the flowprobe around the pulmonary artery. At the conclusion of the experiment a search for intra and extracardiac shunting was done. Pulmonary vascular resistance (PVR) and systemic vascular resistance (SVR) were determined using standard formulas. Gas tensions in arterial blood were determined using a calibrated blood gas analyzer. Gas tensions were corrected for core temperature.

After obtaining baseline hemodynamic measurements, pulmonary hypertension was induced by infusing a thromboxane A2 agonist (U46619) into the femoral venous catheter. The U46619 infusion was titrated to increase and maintain the PVR at 2–3 times baseline measurements. After stable pulmonary hypertension was maintained, the animals received either 2-(dimethylamino)ethylputreanate nonoate (the drug group; n=6) or a placebo (the control group; n=3). For each group, the study drug or placebo was dissolved in 10 mL of bacteriostatic saline and instilled through a 6F feeding tube that had been placed in the endotracheal tube. The tip of the endotracheal tube was placed at mid-trachea.

Figure 4:
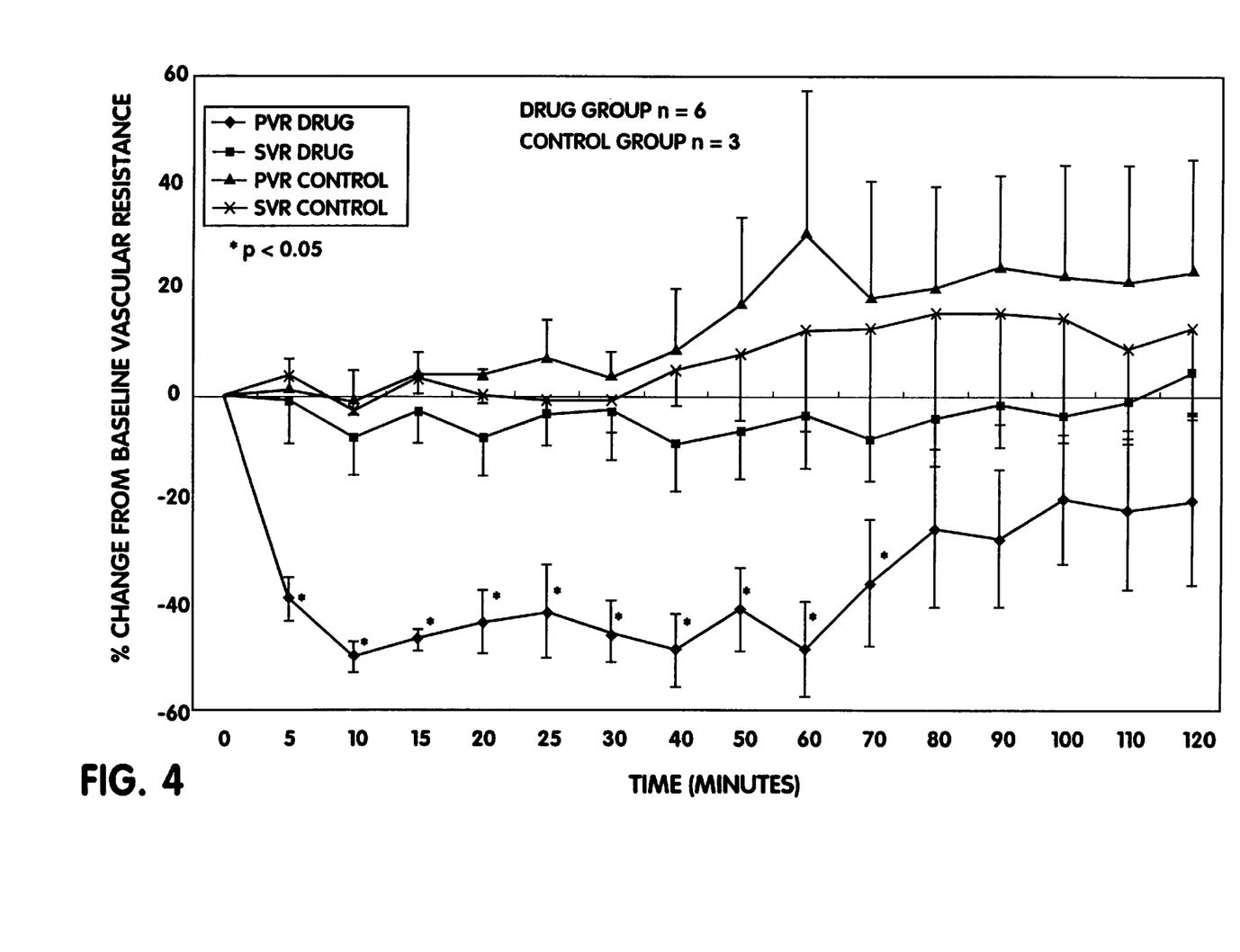
FIG. 4 is a graph of pulmonary vascular resistance (PVR) and systemic vascular resistance (SVR) in treatment and control animals, in an in vivo model of pulmonary hypertension, with the treatment drug being 2-(dimethylamino)ethylputreanate nonoate.

FIG. 4 summarizes the results of the experimental data, showing changes from baseline vascular resistance. Time 0 represents the installation of the study drug. In the animals receiving the study drug, the PVR decreased by 50 to 60% from baseline values. This decrease was statistically significant ($p<0.05$) at each time point until 80 minutes post drug installation. The SVR remained unchanged from baseline in the study drug group. In the animals receiving placebo (control), the PVR and SVR did not change significantly from baseline values. These data demonstrate that the liquid study drug, when delivered into the trachea of an anesthetized animal with pulmonary hypertension, can selectively lower PVR without lowering SVR.

Example 7

2-(dimethylamino)Ethylputreanate Nonoate Effective in Mediating Penile Erection

Four mature male cats weighing 4.0 to 6.0 kg were sedated with ketamine hydrochloride (10 to 15 mg/kg intramuscularly) and anesthetized with sodium pentobarbital (30 mg/kg intravenously). A vertical, circumcision-like incision was made to expose the two ventral *corpora cavernosa* and the dorsal *corpus spongiosum*. A 30-gauge needle was placed into the right corpus to permit administration of the drug into the penis. A 25-gauge needle was placed midway into the left corpus for the measurement of intracavernous pressure. Systemic arterial and intracavernous pressures (mmHg) were measured with Statham P23 transducers connected to a Grass model 7 polygraph zeroed at the right atrial level. Penile length (mm) was measured with a ruler. Animals were divided into two groups, a control group and a drug treatment ("drug") group, with the drug group including four cats. Each of the animals in the drug group received 17 mg drug/0.2 ml normal saline intrautrethrally. The results discussed below are presented as mean values±the standard error of the mean (s.e.m.).

Figure 5A:
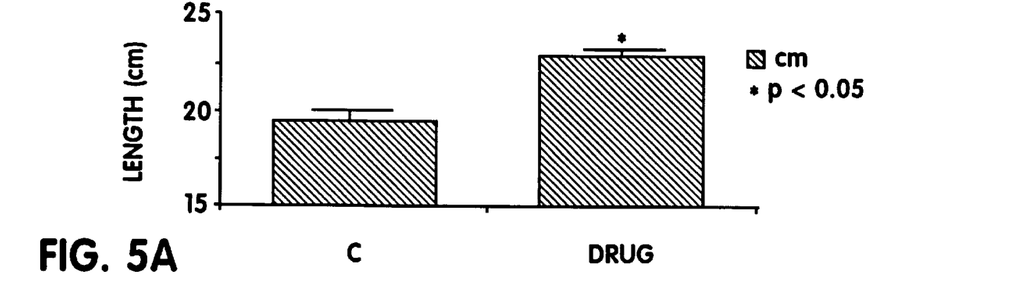
FIGS. 5A–5D are graphs of various parameters for control and treatment animals in an in vivo study of the effect of 2-(dimethylamino)ethylputreanate nonoate on penile erection.
Figure 5B:
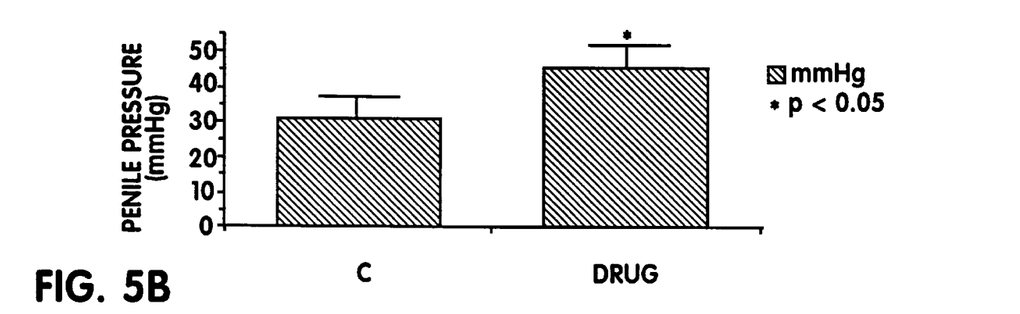
Figure 5C:
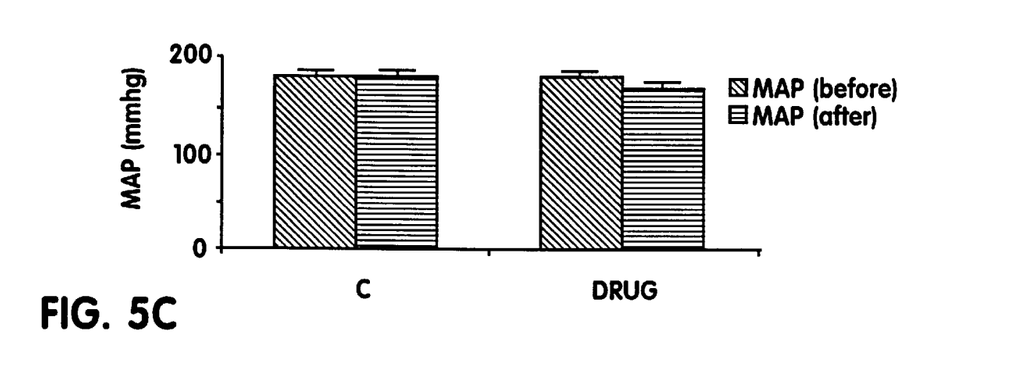
Figure 5D:
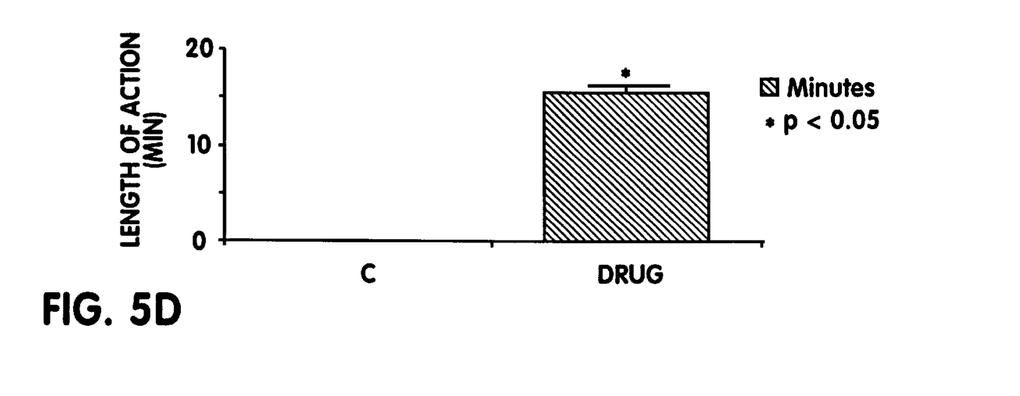

The results shown in FIGS. 5a–5d show that 2-(dimethylamino)ethylputreanate nonoate (the "drug") is effective in mediating penile erection. With reference to FIG. 5a, the animals receiving the drug showed a significant increase in penile length in comparison to the control animals (23±0.3 cm, compared with 19±0.3 cm for the control animals). With reference to FIG. 5b, the animals receiving the treatment drug showed a significant increase in penile pressure after administration of the drug (46±6 mm Hg, compared with 31±6 mm Hg for the control animals). As shown in FIG. 5d, the length of drug action for the treatment animals was approximately 15 minutes (15±2 min). Moreover, these positive treatment results were achieved without a significant fall in mean arterial pressure (MAP) as shown in FIG. 5c. Mean pressure in the control animals remained constant at 182±6 mm Hg. In the animals receiving the treatment drug, MAP dropped from 182±6 mm Hg prior to administration of the drug to 170±8 mm Hg, a fall which was statistically insignificant (p>0.05).

The detailed description presented above discusses several preferred embodiments and aspects of the invention. However, it is not intended to limit the scope of the invention, which is to be determined by the following claims.

What is claimed is:

1. A method of locally dilating blood vessels in a mammal, comprising the step of:

administering a non-polymeric mucosally impermeant nitric oxide donor compound to a specific site of an apical surface of a mucosa of said mammal in an amount effective to locally dilate said blood vessels at said site, said non-polymeric mucosally impermeant nitric oxide donor compound selected form the group consisting of a tertiary amino aliphatic nitric oxide donor compound and a quaternary amino aliphatic nitric oxide donor compound.

2. The method of claim 1 wherein said compound has a structure selected from the group consisting of:

(VI)

(VII)

(VIII)

(IX)

(X)

(XI)

(XII)

or a salt thereof, wherein

X and X' are independently selected from the group consisting of oxygen, alkylene, alkenylene and

;

Y is selected from the group consisting of alkyl and substituted alkyl;

Z is selected from the group consisting of and alkylene;

$R_1$, $R_2$, $R_3$, $R_1'$, $R_2'$, and $R_3'$ are independently alkyl; and n is an integer from 2 to 6.

3. The method of claim 2 wherein X is

4. The method of claim 3 wherein Y is nitrogen-substituted alkyl.

5. The method of claim 4 wherein $R_1$, $R_2$, $R_3$, $R_1'$, $R_2'$, and $R_3'$ are independently alkyl.

6. The method of claim 5 wherein said compound is selected from the group consisting of 2-(dimethylamino) ethylputreanate nonoate, 2-(dimethylamino)ethylputreanate nonoate and the propyl homolog of 2-(dimethylamino) ethylputreanate nonoate.

7. The method of claim 2 wherein Y is nitrogen-substituted alkyl.

8. The method of claim 7 wherein $R_1$, $R_2$, $R_3$, $R_1'$, $R_2'$, and $R_3'$ are independently $C_1$ to $C_3$ alkyl.

9. The method of claim 2 wherein X and X' are independently selected from the group consisting of 10. The method of claim 9 wherein Z is 11. The method of claim 5 wherein $R_1$, $R_2$, $R_3$, $R_1'$, $R_2'$, and $R_3'$ are independently $C_1$ to $C_3$ alkyl.

12. The method of claim 2 wherein Z is

13. The method of claim 1 for inhibiting or treating pulmonary hypertension.

14. The method of claim 13 wherein said compound is administered to a lung of said mammal.

15. The method of claim 14 wherein said compound is administered as an aerosol or a spray.

16. The method of claim 14 wherein said compound is administered at a concentration of from about 1 mg/ml to about 250 mg/ml of said compound to a liquid carrier.

17. The method of claim 16 wherein said compound is administered at a dose of from about 1 mg/kg body weight to about 50 mg/kg body weight.

18. The method of claim 1 for treating male impotence.

19. The method of claim 18 wherein said compound is administered topically or intraurethrally.

20. The method of claim 19 wherein said compound is administered as a hydrophilic gel.

21. The method of claim 19 wherein said compound is administered at a dose of from about 1 mg/kg body weight to about 50 mg/kg body weight.

22. The method of claim 1 for inhibiting or treating vaginal drying.

23. The method of claim 22 wherein said compound is administered topically or intraurethrally.

24. The method of claim 23 wherein said compound is administered as a hydrophilic gel.

25. The method of claim 23 wherein said compound is administered at a dose of from about 1 mg/kg body weight to about 50 mg/kg body weight.

26. The method of claim 1 for stimulating blood flow to an epithelial mucosal surface of the gastrointestinal tract.

27. The method of claim 26 wherein said compound is administered parenterally.

28. The method of claim 1 wherein said compound is administered to the genitalia to serve as an aphrodisiac.

* * * * *

UNITED STATES PATENT AND TRADEMARK OFFICE
Certificate

Patent No. 5,958,427                                            Patented: September 28, 1999

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Dominick C. Roselle, Andrew L. Salzman, Daniel J. Smith, Csaba Szabo, Richard J. Brilli, Brian Jacobs.

Signed and Sealed this Sixteenth Day of May, 2000.

DONALD E. ADAMS, PH. D, J.D.
*Supervisory Patent Examiner*
Technology Center 1600
Art Unit 1627